United States Patent [19]

Hanifl

[11] Patent Number: 4,657,139

[45] Date of Patent: Apr. 14, 1987

[54] CLOSURE FOR A SYRINGE COLLECTION AND DISPOSAL CONTAINER

[75] Inventor: Paul H. Hanifl, Barrington, Ill.

[73] Assignee: Sage Products, Inc., Cary, Ill.

[21] Appl. No.: 781,754

[22] Filed: Sep. 30, 1985

[51] Int. Cl.$^4$ ............................................. B65D 39/02
[52] U.S. Cl. ................................... 220/336; 206/366; 220/253; 222/548
[58] Field of Search ................ 206/1.5, 365, 366, 370, 206/807; 220/253, 336; 222/153, 480, 516, 548, 553

[56] References Cited

U.S. PATENT DOCUMENTS

| | | | |
|---|---|---|---|
| 3,486,665 | 12/1969 | La Croce | 220/253 |
| 4,375,849 | 3/1983 | Hanifl | 206/366 |
| 4,541,541 | 9/1985 | Hickman et al. | 220/253 |

OTHER PUBLICATIONS

Sage Products Inc., Needle Safety Insurance, 1982, 1983 (sales brochure).

*Primary Examiner*—William Price
*Assistant Examiner*—Jimmy G. Foster
*Attorney, Agent, or Firm*—Willian, Brinks, Olds, Hofer, Gilson & Lione, Ltd.

[57] ABSTRACT

A closure for permanently closing a syringe collection and disposal container provides additional protection against injury or accidental contamination from used needles which have been collected and are awaiting disposal. A wheel-shaped cover is used to open and close an access opening in the top of the container. After the container in full, the wheel is rotated to a closed and locked position. The closure comprises a boss formed on the inboard side of the wheel which drops into an aperture formed in the container in the closed and locked position, thereby restraining further movement of the wheel and preventing the container from being reopened.

2 Claims, 10 Drawing Figures

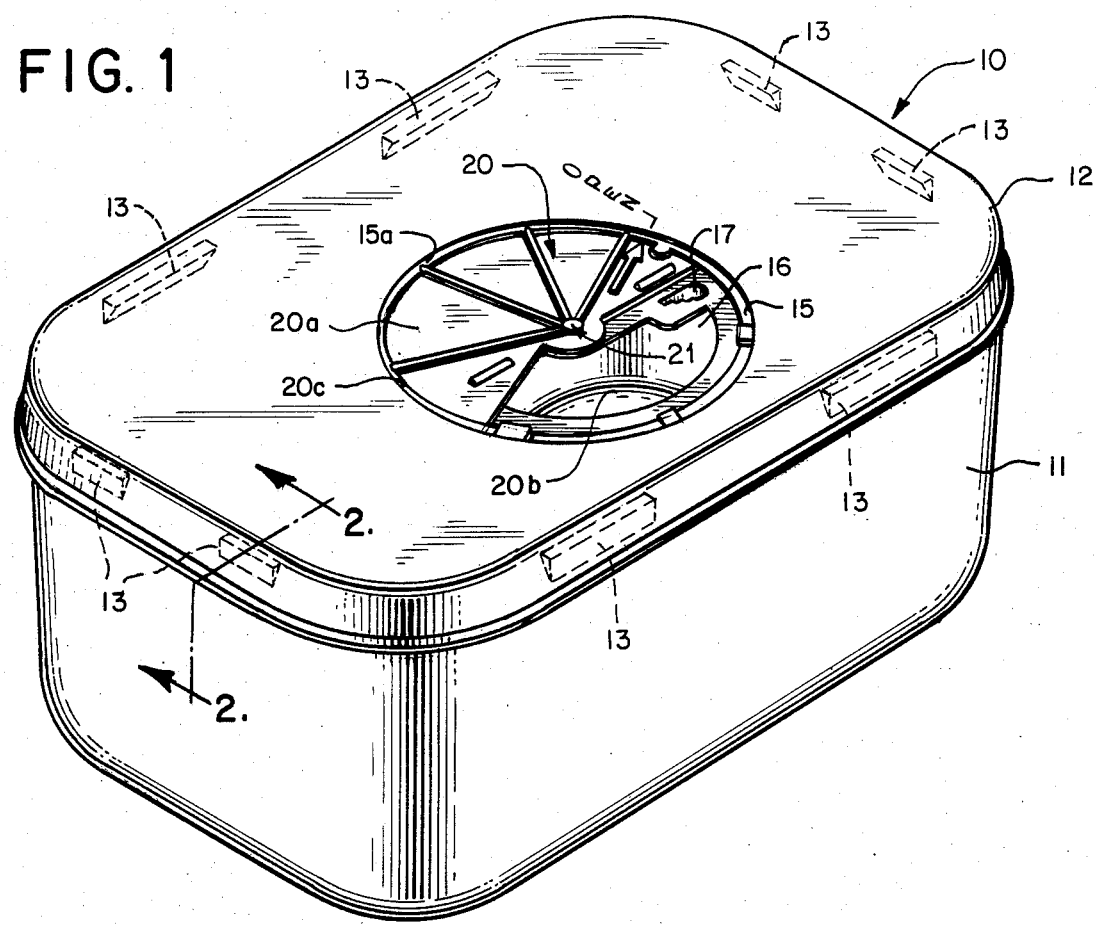
FIG. 1
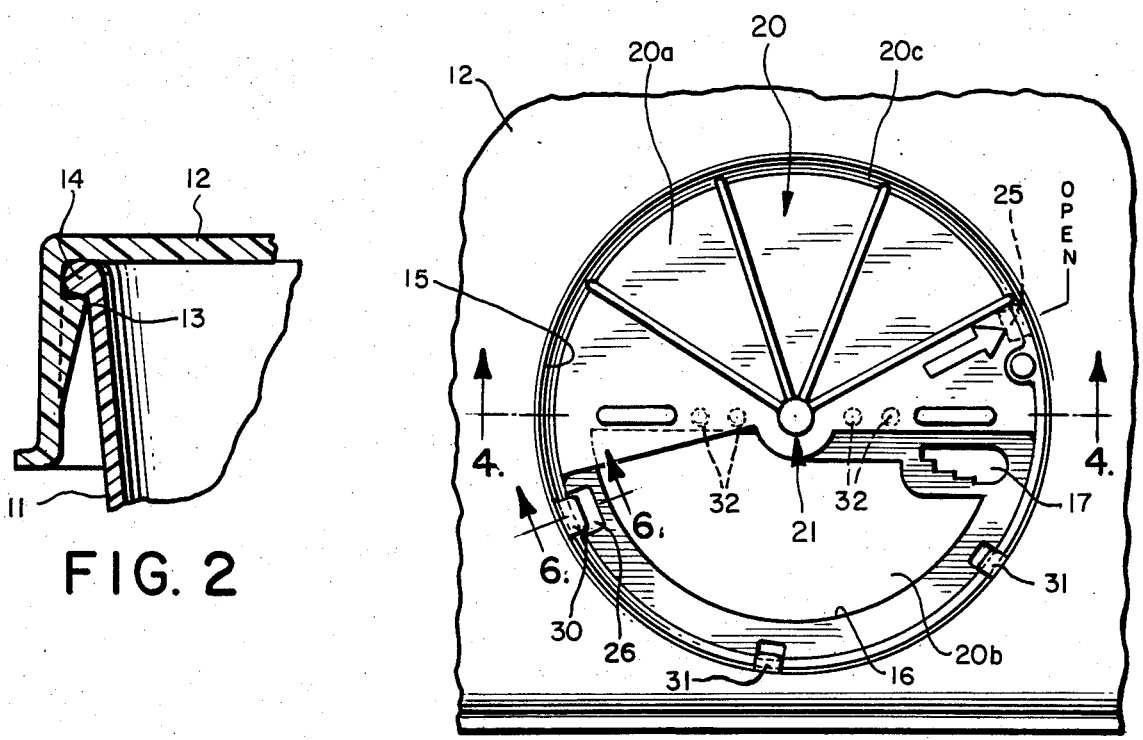
FIG. 2
FIG. 3

CLOSURE FOR A SYRINGE COLLECTION AND DISPOSAL CONTAINER

FIELD OF THE INVENTION

This invention is related to devices for collecting and disposing used needles and syringes, and is particularly directed to a closure for permanently closing an access opening in such a collection and disposal container.

BACKGROUND OF THE INVENTION

The present invention represents an improvement upon the type of syringe needle removal and disposal container disclosed in U.S. Pat. No. 4,375,849, which is also owned by the assignee herein. As that patent points out, a great concern to hospital staff personnel, as well as others in the medical profession, is the safe handling of used needles and syringes, particularly the quick and safe disposal of needles after injection or blood sampling. A serious risk posed to individuals manually handling the used needles is that of skin puncturing or scratching from the sharp end of the needle. Accidents sustained in this manner are believed to be among the most prevalent cause of injury to hospital workers.

The needle removal and disposal container of the U.S. Pat. No. 4,375,849 patent is a novel disposal device for hypodermic injection syringe needles as well as single and double-ended sampling needles, for example. The device enables needles to be quickly and safely removed and disposed of by disengagement of the threaded hub of a needle from the syringe body, with the disengaged needle then being deposited in a storage container, without the used needle ever being manually touched.

Similar containers have been developed for collecting and disposing of not only used needles, but also the entire syringe. That is, the used needle may be separately deposited within the container, or the entire syringe can be passed through an opening provided in the container for collection and ultimate disposal and destruction.

Many containers of the foregoing type utilize a cover in the form of a wheel or rotor-like member for the access opening (or openings) provided in the disposal container. This wheel is rotatable between an open position, wherein the opening in the container is accessible for depositing used needles or the entire syringe into the interior of the container, and a closed position, wherein the opening is closed or covered. A rotary cover is indicated in FIG. 5 of the U.S. Pat. No. 4,375,849 patent, for example.

While such rotory covers are convenient and reasonably effective, there has been no effort made heretofore to provide a locking mechanism for preventing the wheel from being rotated to reopen a full container. Such a locking mechanism for permanently closing the container would be of advantage in preventing a container awaiting disposal from being inadvertently reopened and thereby creating a risk of contamination as well as potential injury from the used needles and syringes collected therein.

SUMMARY OF THE INVENTION

It is a principal objective of this invention to provide an easily operated yet effective closure for permanently closing an access opening defined in a syringe collection and disposal container of the type having a rotary cover for the opening. To this end, the present invention comprises a cover member which is sized to completely cover the container opening. The cover has an inboard side (e.g., top) and an outboard side (e.g., bottom), and is connected to the container at a rotation point adjacent the container opening to permit rotation of the cover member from a first position, wherein the opening is uncovered, to a second position, wherein the opening is completely covered and locked.

A boss is formed on the inboard side of the cover member. This boss is received in a corresponding aperture defined in the container when the cover member is rotated to the second (covered and locked) position. The boss engages in the aperture and prevents the cover member from being rotated from the locked position, thereby permanently closing the disposal container.

In a present form of the invention, the cover member is a rotor or wheel which is formed of a semiflexible material. A bracket or flange element is formed on the container adjacent the boss aperture and overlying the wheel which substantially restrains outboard movement of the wheel when it is rotated to the closed and locked position. An inboard bias is also imposed on the boss by the semiflexible wheel. The bracket and the wheel bias each ensure that the boss completely engages within the aperture so that the wheel is permanently locked closed.

The foregoing features and advantages of the present invention will be more readily understood upon consideration of the following detailed description of the invention taken in conjunction with the accompanying drawings, in which:

BRIEF DESCRIPTION OF THE DRAWINGS

FIG. 1 is a perspective view of a syringe collection and disposal container embodying a closure made in accordance with this invention;

FIG. 2 is an enlarged sectional view taken along line 2—2 of FIG. 1;

FIG. 3 is an enlarged top plan view of the closure and immediately surrounding container lid depicted in FIG. 1;

FIG. 7 is an enlarged sectional view taken along lines 7—7 of FIG. 5a;

DETAILED DESCRIPTION OF THE INVENTION

Figure 4:
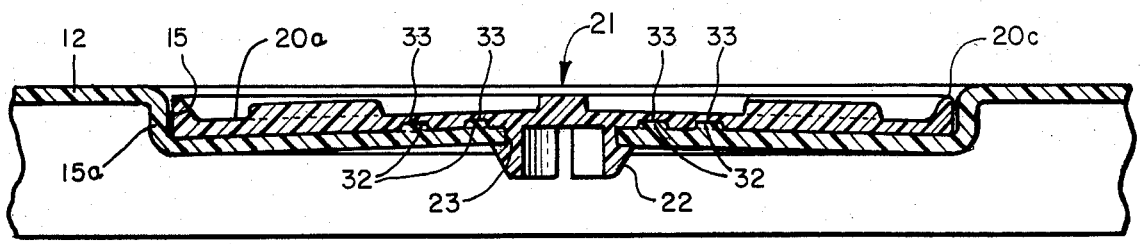
FIG. 4 is an enlarged sectional view taken along line 4—4 of FIG. 3.

A syringe disposal container 10 embodying a closure device made in accordance with the present invention is illustrated in FIG. 1. This is a rigid plastic container having a body portion 11 and a lid 12 which is snap-fitted to the top edge of the main body portion 11. This snap attachment is illustrated in FIG. 2, and is accomplished through the engagement of flange elements 13 with the underside of a bead or lip 14 which surrounds the upper edge of the body portion 11. A well 15 having a small vertical depth defined by circular sidewall 15a is formed in the lid 12 of the container 10. A large access opening 16 is defined within the floor of the well 15, and in this embodiment occupies a little less than one-half of the circular floor area. It is through this opening 16 that portions of the used syringe, or the entire used syringe, may be passed into the interior of the container 10 for collection and ultimate disposal.

In addition to the large opening 16, a mechanism 17 for detaching needles which are screw-threaded to the end of a syringe is also provided in this embodiment, and forms the principal subject matter of the aforementioned U.S. Pat. No. 4,375,849 patent. This needle removing mechanism 17 is also provided on the same half of the well floor as the large opening 16. Reference may be made to the U.S. Pat. No. 4,375,849 patent for further detail concerning the needle removing mechanism 17.

A cover member for both of the openings 16 and 17 takes the form of a rotor or wheel 20. The wheel 20 is attached to the lid 12 within the well 15 at a pivot or rotation point 21, which is centrally located on the well floor. In this embodiment, this connection is made by a stem 22 (FIG. 4) depending from the wheel 20 which snap-fits within an aperture 23 formed in the lid 12 in the center of the well 15. The wheel 20 has a solid portion 20a which takes up more than half of the area of the circular wheel, and an open or cut-out portion 20b. It will be noted that a rim 20c surrounds the outside edge of the wheel 20 and circumscribes both the solid portion 20a and the cut-out portion 20b.

Figure 5A:
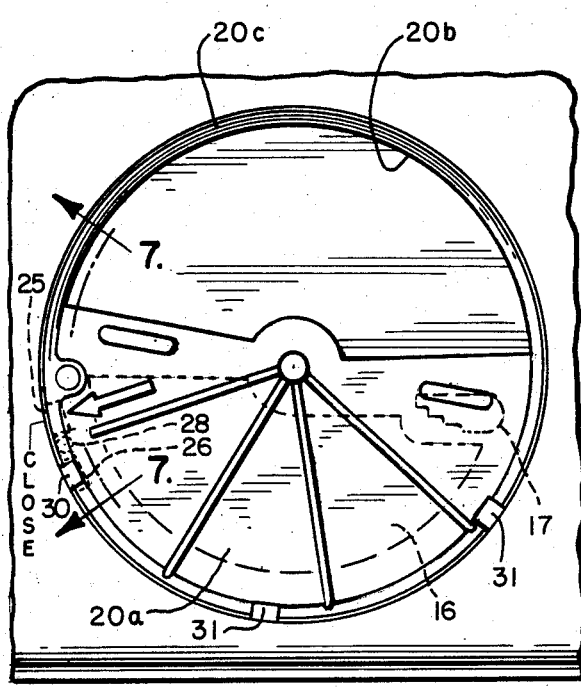
FIGS. 5a and 5b are views similar to that of FIG. 3, showing the cover member in a position where the container opening is covered (5a), and then locked in a closed position (5b)

The syringe disposal container 10 illustrated herein is of a fairly large size, such as would be used in a hospital for collecting needles and syringes over time. The wheel 20 is readily rotatable between an open position, such is illustrated in FIGS. 1 and 3, wherein syringes, needles and the like can be deposited into the interior of the container, to a position where the openings 16, 17 are covered, such as shown in FIG. 5a. After the container 10 is full, the wheel on the container can then be advanced past the closed position illustrated in FIG. 5a to a locked position illustrated in FIG. 5b, wherein the wheel 20 can no longer be rotated. This permanently closes the container 10. The entire syringe disposal container 10 can then be disposed of in a normal manner, such as by burning, melting, etc. With the exception of the closure for permanently locking the wheel in the closed position, all of the foregoing detail concerning the container 10 and the wheel 20 is in the prior art.

Figure 5B:
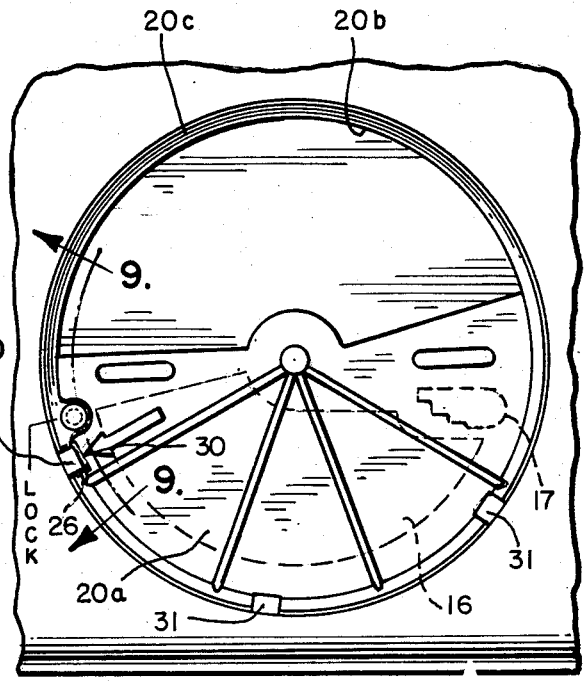

An easily operated and effective closure is provided by this invention which ensures that the wheel 20 will not be rotated from its closed and locked position while awaiting disposal. It serves as an additional safety feature for the container 10 by preventing inadvertent contamination from used needles or injury, such as from a puncture wound, which might occur if the wheel 20 was accidentally rotated uncovering an opening (16 or 17) prior to or during disposal. The closure takes the form herein of a boss 25 formed on the bottom or inboard side of the wheel 20 which engages in an aperture 26 formed in the wheel well 15 when the wheel is rotated to the closed and locked position (FIG. 5b). Once engaged in the aperture 26, the boss 25 cannot be removed therefrom.

Figure 9:
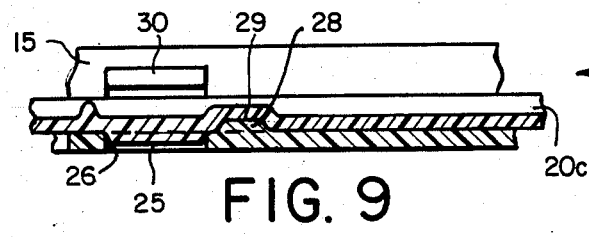
FIG. 9 is an enlarged sectional view taken along line 9—9 of FIG. 5b.

More specifically, the boss 25 is a rectangular protuberance which depends from the bottom or inboard facing side of the wheel 20, and is located adjacent the outside edge of the wheel (see FIG. 5a, for example). The aperture 26 within which the boss 25 is received is also rectangular in shape, but is sized just slightly larger than the perimeter of the boss 25. As illustrated in FIGS. 5b and 9, when the wheel 20 is rotated in a counterclockwise direction (as viewed in FIGS. 1 and 3) to close and lock the wheel against further movement, the boss 25 drops into and engages within the aperture 26. It will be noted that since the boss 25 is formed on the inboard side of the wheel 20, it cannot be accessed once the wheel is rotated to the closed and locked position. The syringe disposal container 10 is thus permanently locked shut in this manner.

Figure 7:
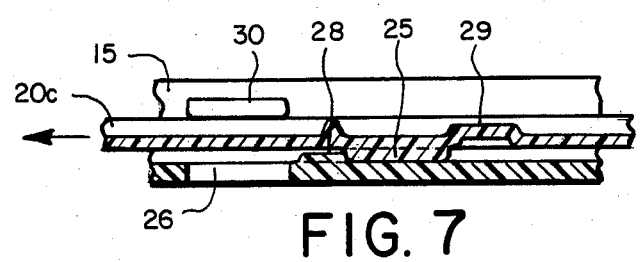

Since it is desirable to open and close the container 10 during use and prior to disposal, a small stop in the form of a dimple 28 is provided on the lid 12 within the well 15 adjacent the aperture 26. As shown in FIG. 5a, the dimple 28 is located slightly clockwise from the aperture 26. When the wheel 20 is rotated to a covered but not locked position (FIG. 5a), the boss 25 can advance as far as the dimple 28 in an unimpeded fashion. When the boss 25 contacts the dimple 28 (FIG. 7), the dimple 28 provides resistance against further movement of the wheel 20 to prevent inadvertent locking of the wheel 20 in the closed position.

Figure 8:
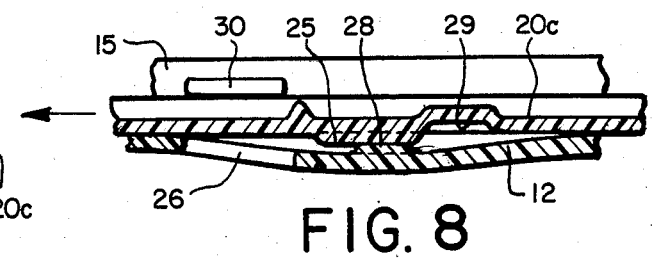
FIG. 8 is an enlarged sectional view similar to that of FIG. 7 showing the cover member slightly more advanced in a counter-clockwise direction (as viewed in FIGS. 5a and 5b)

In order to close and lock the wheel 20, the resistance of the dimple 28 can be readily overcome (FIG. 8), with the boss 25 riding over the dimple 28 to advance into engagement within the aperture 26. Once the boss 25 drops into engagement within the aperture 26, the dimple 28 is received in a like-sized indentation 29 formed in the wheel bottom adjacent the boss 25. Although flexion of the lid 12 is illustrated in FIG. 4 in overcoming the resistance of the dimple 28, the semiflexible wheel 20 could just as well flex outwardly to pass the boss 25 over the dimple 28.

The wheel 20 and the lid 12 in the area of the well 15 cooperate to ensure that the boss 25 fully engages within the aperture 26. FIG. 4 shows that the solid floor of the well 15 is slightly raised in the center. The wheel 20 in turn angles slightly downwardly (as viewed in FIG. 4) from its center, and is urged toward facial engagement with the flat portion of the well floor when in the open position. Complete facial engagement is prevented by the boss 25, however. The semiflexible wheel 20, with its slight inboard curvature, thus tends to bias the boss 25 in an inboard direction. This bias forces the boss 25 downwardly into the aperture 26 when the wheel 20 is in the closed and locked position, and prevents the boss 25 from falling out of the aperture regardless of the orientation of the container 10.

Figure 6:
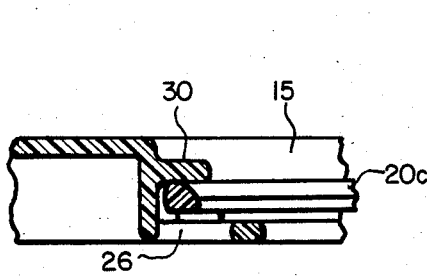
FIG. 6 is an enlarged sectional view taken line 6—6 of FIG. 3.

To further ensure that the boss 25 stays within the aperture 26, a bracket element 30 extends from the well sidewall 15a directly over and substantially parallel to the aperture 26. The bracket element 30 overlies the rim 20c of the wheel 20 (FIG. 6), and restricts the outboard movement of the wheel 20. The bracket element 30 further serves to force the boss 25 in an inboard direction and into the aperture 26, since it forms a restricted "channel" for the rim 20c in this area. This is because the combined vertical thickness of the rim 20c and the boss 25 is greater than the height of this "channel", flexion of the bracket 30 and the floor of well 15 thus forcing the boss 25 into the aperture 26.

It will be noted that similar bracket elements 31 are additionally provided for guiding the wheel rim in the area of the large opening 16 to prevent "gapping" of the solid portion of the wheel 20 with the well floor when in the closed position.

Dimples 32 (FIGS. 3 and 4) are also provided on the floor of wheel well 15 which are received in corresponding detents 33 formed in the bottom of the wheel 20. Engagement of the dimples 32 in the detents 33 serves to keep the wheel 20 in an open position, as illustrated in FIG. 3.

In use, needles, other syringe elements and entire syringes may be deposited within the disposal container 10 through openings 16, 17. When the container is full, the wheel 20 is rotated to a closed and locked position (FIG. 5*b*) wherein the boss 25 engages within the aperture 26. A bias from either or both of the semiflexible wheel 20 and bracket 31 is applied to the boss 25 to maintain this engagement within the aperture 26, permanently closing the container 10. The container 10 can then be disposed of in a conventional manner.

While the invention has been described in connection with a certain presently preferred embodiment, those skilled in the art will recognize many modifications to structure, arrangement, portions, elements, materials and components which can be used in the practice of the invention without departing from the principles of this invention.

What is claimed is:

1. A closure device for permanently closing an opening defined in a syringe collection and disposal container comprising:
   a wheel-shaped cover member having a cut-out portion through which the opening can be accessed and a solid portion sized to completely cover the container opening, said cover member having an inboard side and an outboard side and being connected along its axis of rotation to the container adjacent the container opening in a manner permitting said cover member to be rotated from a first position wherein the opening is accessible through said cut-out portion to a second position wherein the opening is completely covered by said solid portion and said wheel is locked against further rotation,
   a boss formed on the inboard side of said cover member,
   an aperture defined in the container, said boss engaging in said aperture in said second position and preventing rotation of said cover member in any direction, and
   at least one bracket element formed on the container and overlying said aperture, said bracket engaging said outboard side of said cover member to thereby substantially prevent outboard movement of said cover member when said cover member is in said second position, said bracket applying an inboard directed bias to said cover member and boss which forces said boss into engagement with said aperture when in said second position, said cover member thereby being locked in said second position to permanently close the container.

2. The closure device of claim 1 further including a dimple formed on said container adjacent said aperture and in the path of said boss, said dimple being releasably engageable with said boss to thereby prevent inadvertent rotation of said cover member to said second position, said boss riding over said dimple in passing to said second position.

* * * * *